United States Patent
White et al.

(10) Patent No.: US 9,522,860 B2
(45) Date of Patent: Dec. 20, 2016

(54) METHOD AND APPARATUS FOR MANAGING HYDRATE FORMATION IN THE PROCESSING OF A HYDROCARBON STREAM

(75) Inventors: William R. White, Houston, TX (US); James L. Kendall, Houston, TX (US); Jennifer L. Bancroft, Cypress, TX (US); Russell Dean Sellen, Beach City, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 579 days.

(21) Appl. No.: 14/036,722

(22) PCT Filed: Mar. 6, 2012

(86) PCT No.: PCT/US2012/027867
§ 371 (c)(1),
(2), (4) Date: Apr. 9, 2014

(87) PCT Pub. No.: WO2012/141824
PCT Pub. Date: Oct. 18, 2012

(65) Prior Publication Data
US 2014/0296604 A1    Oct. 2, 2014

Related U.S. Application Data

(60) Provisional application No. 61/475,987, filed on Apr. 15, 2011.

(30) Foreign Application Priority Data

Jun. 22, 2011 (EP) .................................. 11170850

(51) Int. Cl.
C07C 7/04 (2006.01)
G06F 9/44 (2006.01)
G06F 9/445 (2006.01)
B01D 3/00 (2006.01)
B01J 6/00 (2006.01)
C07C 4/04 (2006.01)

(52) U.S. Cl.
CPC . *C07C 7/04* (2013.01); *B01D 3/00* (2013.01); *B01J 6/008* (2013.01); *C07C 4/04* (2013.01); *G06F 8/36* (2013.01); *G06F 8/61* (2013.01)

(58) Field of Classification Search
CPC .................................. B01J 6/008; B01D 3/00
USPC ...... 585/638, 800, 539, 6, 400, 15; 206/106, 206/130, 81
See application file for complete search history.

(56) References Cited

U.S. PATENT DOCUMENTS

| | | | |
|---|---|---|---|
| 3,096,383 A * | 7/1963 | Hann | C07C 7/20 208/370 |
| 4,150,962 A | 4/1979 | Colton | |
| 6,566,309 B1 * | 5/2003 | Klug | C08G 65/33303 585/15 |
| 7,943,808 B2 | 5/2011 | Hershkowitz et al. | |
| 2004/0004022 A1 | 1/2004 | Stell et al. | |
| 2004/0004027 A1 | 1/2004 | Spicer et al. | |
| 2007/0191664 A1 | 8/2007 | Hershkowitz et al. | |
| 2008/0300438 A1 | 12/2008 | Keusenkothen et al. | |
| 2009/0008292 A1 | 1/2009 | Keusenkothen et al. | |

FOREIGN PATENT DOCUMENTS

EP    434049    4/1994

* cited by examiner

*Primary Examiner* — Sharon Pregler (57) ABSTRACT

A method and system are disclosed for managing hydrate formation in a process that converts a hydrocarbon stream into $C_2$ unsaturates, such as ethylene and/or acetylenes. The method includes adding a hydrate inhibitor to a hydrocarbon stream to lower the hydrate formation point of the mixture stream from an initial hydrate formation point ($H_I$) of the hydrocarbon stream to a depressed hydrate formation point ($H_D$) of the mixture stream. Then, the mixture stream is depressurized to adiabatically cool the stream to a temperature (T), wherein the $H_D<T<H_I$. Then, at least a portion of the mixture stream is vaporized and the vaporized portion of the mixture stream is separated from the unvaporized portion of the mixture stream. Once separated, at least a portion of the vaporized portion is converted into product, such as ethylene and/or acetylene.

13 Claims, 3 Drawing Sheets

METHOD AND APPARATUS FOR MANAGING HYDRATE FORMATION IN THE PROCESSING OF A HYDROCARBON STREAM

PRIORITY CLAIM

This application is a 371 National Stage Application of International Application No. PCT/US2012/027867, filed Mar. 6, 2012 and European Application No. 11170850.9, filed on Jun. 22 2011, which claims the benefit of Ser. No. 61/475,987, filed Apr. 15, 2011, all of which are incorporated by reference herein in their entirety.

FIELD OF THE INVENTION

The present techniques relate to a method of managing hydrate formation in the processing of a hydrocarbon stream. Further, the present techniques involve a configuration that includes processing a hydrocarbon stream in a manner that provides enhanced operation.

BACKGROUND OF THE INVENTION

The oil and gas industry desires to efficiently obtain and process hydrocarbons into desired products. These processes generally involve the use of thermal changes and/or pressure changes to separate the hydrocarbons in various stages. In particular, the processing may be performed in an oil refinery, which converts or separates the hydrocarbons (e.g., crude oil) into different streams, such as gases, light naphtha, heavy naphtha, kerosene, diesel, atmospheric gas oil, asphalt, petroleum coke and heavy hydrocarbons. Similarly, if the processing is performed in a natural gas refinery, the natural gas may be converted into industrial fuel gas, ethane, propane, butanes and pentanes.

In conventional facilities, different units separate the hydrocarbons into the desired streams. These units may include an atmospheric distillation unit, a vacuum distillation unit, a delayed coker, a hydrotreater, a merox treater, an isomerization unit, a catalytic reformer, a fluid catalytic cracker, an amine treater, a hydrocracker, and a pyrolysis unit, such as a regenerative reactor or steam cracker. Typically, the hydrocarbon stream is passed through the atmospheric distillation unit to divide the hydrocarbons (e.g., crude oil) into gases, naphtha (e.g., light naphtha and heavy naphtha), kerosene/jet fuel, diesel oil, atmospheric gas oil and atmospheric resid or bottoms. As an example, the volume amounts of these separated products or streams may be gases of 5 weight percent (wt %), naphtha of 20 wt % to 30 wt %, kerosene/jet fuel 5 wt % to 20 wt %, diesel oil of 15 wt % to 20 wt %, atmospheric gas oil of 20 wt % to 30 wt %, and atmospheric resid or bottoms of 5 wt % to 20 wt %. Each of the different percentages being a specific portion of the hydrocarbon feed. The amount of these different products may vary based on the different crude oil provided for processing in the system. Some other conventional refinery facilities may also include a vacuum distillation unit, a hydrotreater, a merox treater, a delayed coker, a fluid catalytic cracker and a hydrocracker, which are used to further separate products, such as light vacuum gas oil, heavy vacuum gas oil and vacuum residuum.

Once the hydrocarbons have been separated, pyrolysis units are typically used to further process certain of the hydrocarbon streams to produce olefins. Olefins are the basic building block for other petrochemical products, which may be utilized to produce other products. As a specific example, a pyrolysis unit may be a steam cracking furnace that may convert ethane into ethylene and other byproducts. The ethylene may be separated from the by products and further processed into polyethylene or other products.

As part of the processing of the hydrocarbon stream, the hydrocarbons may have to be transported via conduits and/or pipes to the pyrolysis unit. That is, the hydrocarbon stream may be provided via a pipeline to the facility or via conduits and/or pipes at another location within the facility. As an example, if the hydrocarbon stream is an ethane stream, it may be transported via a pipeline grid system at high pressure (e.g., about 900 psig (pounds per square inch gauge) (6205 kilopascal gauge (kPag)) in the super critical state. This high pressure ethane stream may also be referred to as dense phase ethane. If the hydrocarbon stream is provided at this higher pressure, it may have to be depressurized prior to being fed to a pyrolysis unit.

While some hydrocarbon processes use methanol in cold environments to remove hydrates (e.g., referred to as deriming), conventional processes for transporting hydrocarbons and depressurizing the hydrocarbons upstream of a pyrolysis unit do not utilize hydrate suppression to manage the hydrates. Commonly, the higher pressure hydrocarbon streams are either vaporized using low pressure steam prior to being provided to a pyrolysis unit or the processes utilize driers to remove the water from the hydrocarbon stream before letting down in pressure, which reduces the temperature of the hydrocarbon stream. The removal of the water prevents freezing problems and hydrate formation, as the temperature may be below the hydrate formation point for the hydrocarbon stream. Hydrates are solid crystalline products, which form when water encages hydrocarbon molecules, such as ethane. In certain instances, hydrates may form at temperatures well above the freezing point of water. As an example, for ethane, the initial hydrate formation point is between 60° F. (15.5° C.) and 65° F. (18.3° C.), which is dependent upon the specific pressure. Similar to ice formed from water, hydrates from the hydrocarbon stream may plug pipelines and other process equipment resulting in shutdowns and other operational problems.

Hydrate suppression is commonly used in the processing of natural gas liquid (NGL). See Gas Conditioning and Processing, Volume 1: The Basic Principles, by John M. Campbell. In natural gas liquid processes, the wet natural gas is cooled to separate the dry natural gas from water. The hydrate inhibitor enables operating at colder temperatures than the stream alone. This process utilizes cooling of the natural gas liquid stream to assist the separation, which is not useful in the proposed process.

What is needed is a method for managing hydrate formation in a hydrocarbon stream for a pyrolysis unit, such as a steam cracking furnace or a regenerative reverse flow reactor. In particular, it may be desirable to construct a system that manages a hydrocarbon stream for a pyrolysis unit in more efficient manner, which manages the hydrate formation through the process.

SUMMARY OF THE INVENTION

The present techniques provide a process to manage hydrate formation in a hydrocarbon stream. In an embodiment, a method of processing a hydrocarbon stream is described. The method comprises providing a hydrocarbon stream having an initial hydrate formation point ($H_I$); adding a hydrate inhibitor to the hydrocarbon stream to form a mixture stream and lower the hydrate formation point from the initial hydrate formation point ($H_I$) of the hydrocarbon stream to a depressed hydrate formation point ($H_D$) of the mixture stream; depressurizing the mixture stream to adiabatically cool the mixture stream to a temperature (T), wherein the $H_D<T<H_I$; vaporizing at least a portion of the mixture stream; and separating a first product that includes at least a portion of the vaporized portion of the mixture stream from a second product that includes at least a portion of the unvaporized portion of the mixture stream.

The method may further include passing the mixture stream through a static mixer to intermingle the compounds in the mixture stream upstream of the depressurizing; vaporizing at least a portion of the hydrocarbons in the stream upstream of the separating and downstream of the depressurizing; and/or processing (e.g., cracking) at least a portion of the first product to produce $C_2$ unsaturates in a pyrolysis reactor.

In another embodiment, a hydrocarbon processing system is described. The system includes a mixing unit configured to receive a hydrocarbon stream and a hydrate inhibitor and combine the streams together into a mixture stream; a depressurization unit in fluid communication with the mixing unit and configured to reduce the pressure of the mixture steam; a vaporization unit in fluid communication with the depressurization unit and configured to vaporize at least a portion of the hydrocarbons in the depressurized mixture stream via thermal exposure; and a separation unit in fluid communication with the vaporization unit and configured to separate a first product comprising at least a portion of the vaporized hydrocarbons in the depressurized mixture stream and a second product comprising the hydrate inhibitor. The separation unit and the vaporization unit may be located in the same vessel (e.g., as a hybrid vessel). The system may also include a pyrolysis unit downstream of and in fluid communication with the separation unit and configured to process (e.g., crack) at least a portion of the first product into effluent comprising $C_2$ unsaturates, a heat exchanger downstream of the mixing unit, upstream of the depressurization unit and in fluid communication with the mixing unit and the depressurization unit, wherein the heat exchanger is configured to cool the mixture stream via indirect heat transfer with a utility fluid. The utility fluid may comprise at least a portion of the first product and the heat exchanger is configured to heat the first product upstream of a pyrolysis unit.

In certain other embodiments, the method or system may include cooling the mixture stream by passing the mixture stream through a first side of a heat exchanger; and heating the at least a portion of the first product upstream of the cracking by passing at least a portion of the first product through a second side of a heat exchanger. The cracking may involve heating the at least a portion of the first product to temperatures in the range of 500° C. to 880° C. or in the range of 1200° C. to 2000° C. to produce the $C_2$ unsaturates. The hydrocarbon stream may be provided at a pressure in the range of 700 psia to 1100 psia (4826 kPaa to 7584 kPaa), and may be reduced to pressure in the range of 50 psia to 400 psia (345 kPaa to 2758 kPaa). Also, the depressurizing may involve reducing the temperature of the mixture stream to a temperature in the range of 20° F. to −20° F. (−6.7° C. to −28.9° C.). The hydrocarbon stream comprises equal to or greater than (≥)90 wt % ethane, wherein the vaporizing comprises heating the mixture stream to vaporize ≥90 wt % of the ethane in the mixture stream, or may include ≥90 wt % methane. Also, the hydrate inhibitor may have a concentration of thermodynamic inhibitor that is in the range of 60 wt % to 90 wt % or 100 wt % of the hydrate inhibitor, wherein the hydrate inhibitor comprises one or more of mono-ethylene glycol (MEG) and tri-ethylene glycol (TEG).

In yet other embodiments, the system or method may include different control mechanisms. The control mechanism may include a process control unit in communication with one or more control units and one or more measurement devices, wherein the process control unit is configured to adjust an amount of thermodynamic inhibitor in the hydrate inhibitor. The one or more measurement devices is coupled to a line upstream of an inlet or at the inlet of the depressurization unit and configured to communicate pressure data to the process control unit. The process control unit includes a processor, set of instructions stored in memory and when executed by a processor are configured to: (i) receive the pressure data; (ii) determine an amount of the thermodynamic inhibitor in the hydrate inhibitor; and (iii) indicate an adjustment of the amount of the thermodynamic inhibitor in the hydrate inhibitor.

The invention will be described in connection with its preferred embodiments of the present techniques. However, to the extent that the following detailed description is specific to a particular embodiment or a particular use, this is intended to be illustrative only, and is not to be construed as limiting the scope of the invention. On the contrary, it is intended to cover all alternatives, modifications and equivalents that may be included within the spirit and scope of the invention, as defined by the appended claims.

DETAILED DESCRIPTION OF THE INVENTION

The present techniques relate to a method and configuration of managing hydrate formation in a hydrocarbon stream. That is, the present techniques relate to a hydrocarbon stream processing method that utilizes hydrate suppression to enhance olefin recovery. Specifically, the present techniques provide an enhanced method and configuration that manages recovery of refrigeration used with the hydrocarbon streams, such as dense phase ethane or dense phase methane, by using hydrate suppression instead of process driers in front of the cryogenic exchangers. That is, the present techniques add a hydrate inhibitor that is mixed with the hydrocarbon stream prior to expansion and vaporization of the mixture stream. The hydrate inhibitor may include a specific concentration of a thermodynamic inhibitor, which may be all thermodynamic inhibitor or a mixture with another fluid, such as water. The hydrate inhibitor lowers the initial hydrate formation point ($H_I$) of the hydrocarbon stream to a depressed hydrate formation point ($H_D$) of the mixture stream. Then, at least a portion of the thermodynamic inhibitor is removed from the mixture stream and the hydrocarbons are passed to a pyrolysis unit for conversion into various products, such as ethylene, acetylene, for example. The depressurization of the mixture stream may vaporize at least a portion of the mixture stream and adiabatically cool the mixture stream to a temperature (T), wherein the $H_D<T<H_I$. In this embodiment, at least a portion of the hydrate inhibitor may be recycled to enhance the efficiency of the process. Accordingly, the process may provide an alternative to other approaches that utilize driers upstream of the cryogenic services for a hydrocarbon stream.

To provide the appropriate concentration of thermodynamic inhibitor, the present techniques may monitor certain operational parameters and adjust operational settings to provide an enhanced process. That is, the operational settings (e.g., position of a valve and/or flow rate control device, for example) may be adjusted to manage the amount of hydrate inhibitor or even the amount of thermodynamic inhibitor in the hydrate inhibitor to be added to the hydrocarbon stream within the system and to manage hydrate formation. The operational settings may be adjusted to manage hydrate formation based on measured operational parameters, which may include measured values that are stored as operational data in the memory, and utilized by a processor to communicate an adjustment to an operational setting. The present techniques may be further understood with reference with the FIGS. 1-3, which are discussed below.

Unless otherwise stated, all percentages, parts, ratios, etc., are by weight. Unless otherwise stated, a reference to a compound or component includes the compound or component by itself, as well as in combination with other compounds or components, such as mixtures of compounds.

Further, when an amount, concentration, or other value or parameter is given as a list of upper preferable values and lower preferable values, this is to be understood as specifically disclosing all ranges formed from any pair of an upper preferred value and a lower preferred value, regardless whether ranges are separately disclosed.

The terms "convert," "converting," "crack," and "cracking" are defined broadly herein to include any molecular decomposition, breaking apart, conversion, dehydrogenation, and/or reformation of hydrocarbon or other organic molecules, by means of at least pyrolysis heat, and may optionally include supplementation by one or more processes of catalysis, hydrogenation, diluents, stripping agents, and/or related processes.

The term "nominal final boiling point" shall mean the temperature at which 99.5 wt % of a particular sample has reached its boiling point.

The term "hydrate formation point" is a division point for a given stream between process conditions when hydrates form for a given pressure and temperature. That is, hydrates form when a fluid stream is colder than its water dew point for a given pressure and temperature. Hydrates are a structure of a water lattice in which light hydrocarbon molecules are embedded. These hydrates typically form when a stream is cooled below its hydrate formation temperature in the presence of free water for a given pressure (i.e. the gas is colder than its water dew point temperature).

Figure 1:
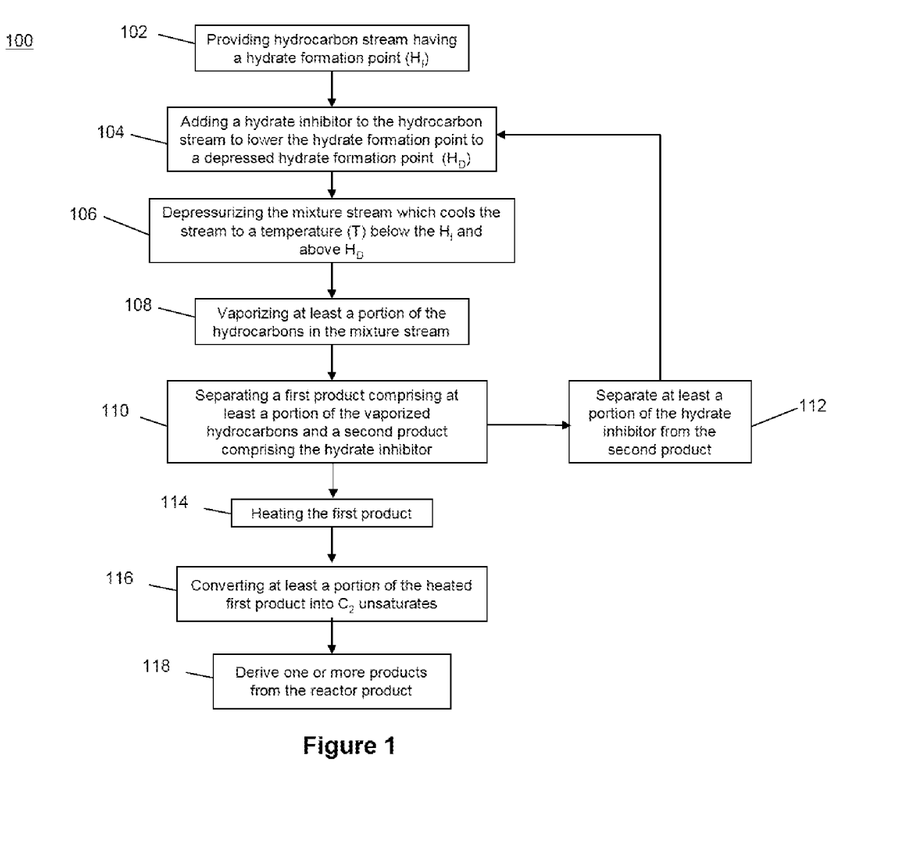
FIG. 1 is a block flow diagram relating to a method for processing a hydrocarbon stream to produce products according to an exemplary embodiment of the present techniques.

To begin, an exemplary embodiment of the present techniques is illustrated in the block flow diagram 100 of FIG. 1. In this flow diagram 100, a process for managing hydrate formation in the processing of a hydrocarbon stream into $C_2$ unsaturates (e.g., ethylene and/or acetylene) is described. As part of the process, a hydrate inhibitor may be added to a hydrocarbon stream to lower the hydrate formation point of the resulting mixture stream from an initial hydrate formation point ($H_I$) of the hydrocarbon stream to a depressed hydrate formation point ($H_D$) of the mixture stream. The resulting mixture stream may then be depressurized to a sufficient level to adiabatically cool the mixture stream to a temperature (T), wherein the $H_D<T<H_I$. Optionally, the depressurizing step may be to a sufficient level to vaporize at least a portion of the mixture stream. The depressurized mixture stream can be heated to a temperature that vaporizes at least a portion of the mixture stream. Then, the vaporized portion of the mixture stream may be further processed into products, such as ethylene, acetylene, polyethylene or other products. The unvaporized portion of the mixture stream may also be further processed, which may involve recovering the hydrate inhibitor and/or thermodynamic inhibitor for recycling in the process.

A hydrocarbon stream is provided at block 102. The hydrocarbon stream may include one or more of methane, ethane, propane and mixtures thereof. At least a portion of the hydrocarbon feed may have a nominal end boiling point of at least −205° F. (−131.7° C.) at 100 psia (pounds per square inch absolute) (689 kilopascal absolute (kPaa)), at least −47° F. (−43.9° C.) at 100 psia (689 kPaa), or at least 55° F. (12.8° C.) at 100 psia (689 kPaa). The hydrocarbon stream may include ≥50 weight percent (wt %) ethane, ≥70 wt % ethane, ≥90 wt % ethane, or ≥95 wt % ethane. The remaining portion of the hydrocarbon stream may include methane, propane, or mixtures thereof. That is, the hydrocarbon stream may include methane, propane, or a mixture thereof in an amount in the range of 1 wt % and 50 wt %, in the range of 1 wt % and 30 wt %, in the range of 1 wt % and 10 wt %, or in the range of 1 wt % and 5 wt %, with the remainder comprising ethane. In other embodiments, the hydrocarbon stream may include 25 wt % methane, greater than 70 wt % methane, greater than 90 wt % methane, or even greater than 95 wt % methane. Further, the temperatures of the hydrocarbon stream may include temperatures greater than 75° F. (23.9° C.), greater than 65° F. (18.3° C.), in the range of 100° F. to 60° F. (37.8° C. to 15.5° C.), or in the range of 70° F. to 60° F. (21.1° C. to 15.5° C.), while the pressure of the hydrocarbon stream may include pressures greater than 400 psia (2758 kPaa), greater than 600 psia (4137 kPaa), greater than 800 psia (5516 kPaa), in the range of 400 psia to 2000 psia (2758 kPaa to 13790 kPaa), in the range of 600 psia to 1500 psia (4137 kPaa to 10342 kPaa), in the range of 700 psia to 1100 psia (4826 kPaa to 7584 kPaa), or in the range of 800 psia to 950 psia (5516 kPaa to 6550 kPaa).

At block 104, a hydrate inhibitor may be added to the hydrocarbon stream, wherein the mixture may be referred to as a mixture stream. The hydrate inhibitor may be recycled, as noted below, or from a source that has not passed through the process. Regardless, the hydrate inhibitor may be added, preferably via a mixing unit, which may be a joint between two pipes, a static mixer, a nozzle within a unit or portion of the heat exchanger, or other suitable unit. The addition of the hydrate inhibitor with the hydrocarbon stream may be performed at process conditions (e.g., temperatures and/or pressures) above or near the hydrate formation point for the hydrocarbon stream. The temperatures may include temperatures in the range of 100° F. to 40° F. (37.8° C. to 4.4° C.), in the range of 80° F. to 50° F. (26.7° C. to 10° C.), or in the range of 70° F. to 58° F. (21.1° C. to 14.4° C.), while the pressure may be near or above those of the hydrocarbon stream. The amount of hydrate inhibitor in the mixture stream may include amounts in the range of 0.1 wt % and 10 wt %, in the range of 0.3 wt % and 5 wt %, in the range of 0.5 wt % and 4 wt %. The amount of thermodynamic inhibitor in the hydrate inhibitor may vary, as noted further below.

The hydrate inhibitor may comprise thermodynamic inhibitors combined into a mixture with water, hydrocarbons, or other suitable fluid. Thermodynamic inhibitors are described as being utilized in natural gas liquids (NGL) processing to enable operating below the dew point for NGL stream alone. See Gas Conditioning and Processing, Volume 1: The Basic Principles, by John M. Campbell, specifically pages 119-122. The thermodynamic inhibitors shift the process conditions (e.g., temperature and pressure) at which hydrates are stable from an initial hydrate formation point ($H_I$) to a depressed hydrate formation point ($H_D$). The thermodynamic inhibitors may include methanol and various glycols such as mono-ethylene glycol (MEG) and tri-ethylene glycol (TEG), for example.

The amount of thermodynamic inhibitors in the hydrate inhibitor may be adjusted to provide adequate thermodynamic inhibitor for any water in the mixture stream (e.g., water in the hydrocarbon stream along with any water in the hydrate inhibitor). In an embodiment, the amount of water in the hydrate inhibitor may greatly exceed the amount of water in the hydrocarbon stream. A ratio of water in the hydrate inhibitor to water in the hydrocarbon stream may be ≥30:1, ≥40:1, in range of 30:1 to 70:1, or even in range of 40:1 to 60:1. As a result, the concentration of the thermodynamic inhibitor in the hydrate inhibitor may control the temperature drop for the system because the water in the hydrocarbon stream is significantly smaller than the water in the hydrate inhibitor. Alternatively, as another embodiment, the hydrate inhibitor may include little to no water (e.g., substantially thermodynamic inhibitor). A ratio of water in the hydrate inhibitor to water in the hydrocarbon stream may be less than or equal to (≤)20:1, ≤10:1, in range of 20:1 to 1:1, or even in range of 10:1 to 2:1. Accordingly, the amount of water present in the hydrocarbon steam is water (e.g., being substantially the total water of the mixture stream) that has to be managed in the mixture stream by the thermodynamic inhibitor. As a result for this configuration, the concentration of the thermodynamic inhibitor in the hydrate inhibitor has to be managed to control the temperature drop, which is primarily based on the water in the hydrocarbon stream. While the hydrate inhibitors are discussed further in FIGS. 2 and 3, the amount of thermodynamic inhibitors in the hydrate inhibitor may include amounts in the range of 1 wt % and 100 wt %, in the range of 40 wt % and 80 wt %, in the range of 50 wt % and 70 wt %, in the range of 60 wt % and 90 wt %, or in the range of 60 wt % and 100 wt %, while the remaining amount may include water, hydrocarbons, or other suitable fluid.

At block 106, the mixture stream is depressurized to adiabatically cool the mixture stream temperature (T) to a point that is between the initial hydrate formation point ($H_I$) and the depressed hydrate formation point ($H_D$) (e.g., $H_D<T<H_I$). The depressurization may be performed in one or more depressurization units, turbo expansion devices and/or other suitable devices. The "cold" point in the process is at a location that has the coldest temperature (e.g., the location with the greatest potential for hydrate formation), which sets the required thermodynamic inhibitor concentration in the hydrate inhibitor. The mixture stream may be cooled to temperatures in the range of 60° F. to −50° F. (15.5° C. to −45.6° C.), in the range of 40° F. to −30° F. (4.4° C. to −34.4° C.), or in the range of 20° F. to −20° F. (−6.7° C. to −28.9° C.). The pressures involved in the depressurization of the mixture stream may include pressures in the range of 15 psia to 2000 psia (103 kPaa to 13790 kPaa), in the range of 15 psia to 600 psia (103 kPaa to 4137 kPaa), in the range of 50 psia to 900 psia (345 kPaa to 6205 kPaa), in the range of 50 psia to 400 psia (345 kPaa to 2758 kPaa), in the range of 72 psia to 400 psia (496 kPaa to 2758 kPaa), or in the range of 100 psia to 300 psia (689 kPaa to 2068 kPaa). The depressurizing may partially vaporize the mixture stream and it may begin to auto-refrigerate.

In an embodiment, the mixture stream may be subjected to cooling upstream of the depressurization, which may include one or more cooling units, heat exchangers and/or other suitable devices. For example, a heat exchanger may be integrated with other processes, integrated with a feed for the pyrolysis unit, or integrated with units in the pyrolysis system, such as associated with the pyrolysis unit, which is described further below.

Once depressurized, at least a portion of the hydrocarbons in the mixture stream may be vaporized, as shown in block 108. The vaporization may include heating the mixture stream or reducing pressure to process conditions that result in a portion of the hydrocarbons in the mixture stream vaporizing, which may be performed in one or more units. The vaporization may be performed in one or more vaporizers, heat exchangers, pyrolysis units, other suitable devices and/or combinations thereof. The vaporization may be performed at process conditions that vaporize a substantial amount of the hydrocarbons in the mixture stream. For example, the process conditions may be set to vaporize ≥50 wt % of the hydrocarbons in the mixture stream, ≥75 wt % of the hydrocarbons in the mixture stream, ≥85 wt % of the hydrocarbons in the mixture stream, ≥90 wt % of the hydrocarbons in the mixture stream, ≥95 wt % of the hydrocarbons in the mixture stream, or ≥99 wt % of the hydrocarbons in the mixture stream. The process conditions may be adjusted based on the composition of the mixture stream or preferred hydrocarbons to be separated. The vaporization may include heating the mixture stream to temperatures in the range of 30° F. to −30° F. (−1.1° C. to −34.4° C.), in the range of 20° F. to −20° F. (−6.7° C. to −28.9° C.), or in the range of 15° F. to −10° F. (−9.4° C. to −23.3° C.). If the vaporization is performed with a heat exchanger, it may be integrated with other processes, integrated with a feed for the pyrolysis unit, or integrated with units in the pyrolysis system, such as associated with the pyrolysis unit, which is described further below.

Once vaporized, the mixture stream may be separated into a first product comprising at least a portion of the vaporized hydrocarbons in the stream and a second product comprising the hydrate inhibitor and other fluids, as shown in block 110. The separation may be performed in one or more vaporization units, a liquid vapor separator, flash drum, other suitable unit, or combinations thereof. The first product may include ≥50 wt % of the hydrocarbons in the stream, ≥75 wt % of the hydrocarbons in the stream, ≥85 wt % of the hydrocarbons in the stream, ≥90 wt % of the hydrocarbons in the stream, ≥95 wt % of the hydrocarbons in the stream, or ≥99 wt % of the hydrocarbons in the stream. The second product may include ≥90 wt % of the water in the stream, ≥95 wt % of the water in the stream, ≥99 wt % of the water in the stream. Also, the second product may include ≥90 wt % of the hydrate inhibitor in the stream, ≥95 wt % of the hydrate inhibitor in the stream, ≥99 wt % of the hydrate inhibitor in the stream.

In block 112, at least a portion of the hydrate inhibitor or thermodynamic inhibitor may be separated from the second product (e.g., the remaining non-vaporized portion of the mixture stream). This separation may include heating the second product to separate the water and other products from the thermodynamic inhibitor in the second product. The separation may include one or more boilers, vapor-liquid separators, heat exchangers and other suitable units. For example, the water may be vaporized to separate the thermodynamic inhibitor from the second product. In particular, if the thermodynamic inhibitor is MEG, the temperatures may be in the range of 250° F. to 300° F. (121.1° C. to 148.9° C.), while if the thermodynamic inhibitor is TEG, the temperatures may be in the range of 300° F. to 400° F. (148.9° C. to 204.4° C.). If the vaporization is performed with a heat exchanger, it may be integrated with other processes, or integrated with units in the pyrolysis system, such as associated with the pyrolysis unit, which is described further below.

In block 114, the first product, which is at least a portion of the vaporized hydrocarbons from the mixture stream, is further heated prior to being provided to the pyrolysis unit. The heating of the first product may include one or more heat exchangers, boilers, or other suitable devices. Again, if the heat is performed with a heat exchanger, it may be integrated with other processes, or integrated with other units in the pyrolysis system, such as associated with the pyrolysis unit, which is described further below. For example, the first product may be heated to temperatures in the range of −20° F. to 400° F. (−28.9° C. to 204.4° C.), in the range of 10° F. to 300° F. (−12.2° C. to 148.9° C.), in the range of 0° F. to 60° F. (−17.8° C. to 15.5° C.) or in the range of 20° F. to 100° F. (−6.7° C. to 37.8° C.).

Then, at block 116, at least a portion of the heated first product is converted into product, such as ethylene, acetylene, for example. This conversion may include pyrolysis units, such as a steam cracking furnace, partial oxidation reactor, regenerative reverse flow reactor or other suitable pyrolysis unit, which may or may not include a catalyst. Examples of such pyrolysis units and systems may include U.S. Patent App. Pub. No. 20040004022, 20040004027; 20070191664; 20080300438 and/or 20090008292. Further, depending on the pyrolysis unit and the composition of the at least a portion of the first product may be heated to temperatures in the range of 500° C. to 880° C., in the range of 788° C. to 880° C., in the range of 1200° C. to 2000° C., or in the range of 1500° C. to 1800° C. The pressures in the range of 15 psia to 600 psia (103 kPaa to 4137 kPaa), in the range of 50 psia to 400 psia (345 kPaa to 2758 kPaa), in the range of 100 psia to 300 psia (689 kPaa to 2068 kPaa).

At block 118, one or more products may be derived from the pyrolysis or reactor product. These products may include $C_2$ unsaturates, such as ethylene, acetylene and other products. The reactor product may include ethylene in amounts in the range of 1 wt % and 95 wt %, in the range of 30 wt % and 90 wt %, in the range of 40 wt % and 80 wt %. Alternatively, the reactor product may include acetylene in amounts in the range of 1 wt % and 95 wt %, in the range of 30 wt % and 90 wt %, in the range of 40 wt % and 80 wt %. These products may be further processed to provide polyethylene, polypropylene and/or other products.

Beneficially, the process provides an efficient mechanism to manage hydrate formation in the hydrocarbon stream. That is, water does not have to be removed from the process, prior to the depressurization step (e.g., the "cold point") as the hydrate inhibitor lowers the hydrate formation point below the temperatures that the stream is exposed to within the process. As a result, the process does not involve or require driers, which are commonly utilized in such processes. This results in a simplified and enhanced process, which lowers the operation and installation costs.

Further, in an embodiment, heat exchangers may be integrated in the process to provide additional energy savings. For example, in an embodiment, the hydrocarbon stream is cooled prior to the step of depressurizing the mixture stream. This cooling step may occur in a heat exchanger that is integrated with the heating step of block 114. That is, with additional integration within the system, the heat exchangers may be utilized to cool and heat different streams in an effective manner, not provided by other processes. Also, the proposed process may reduce the energy waste with drier configurations. This process provides flexibility in the management of the energy recovery. The hydrate inhibitor may be removed from the process once the temperature of the mixture stream is above the hydrate formation point for the hydrocarbon stream.

Figure 2:
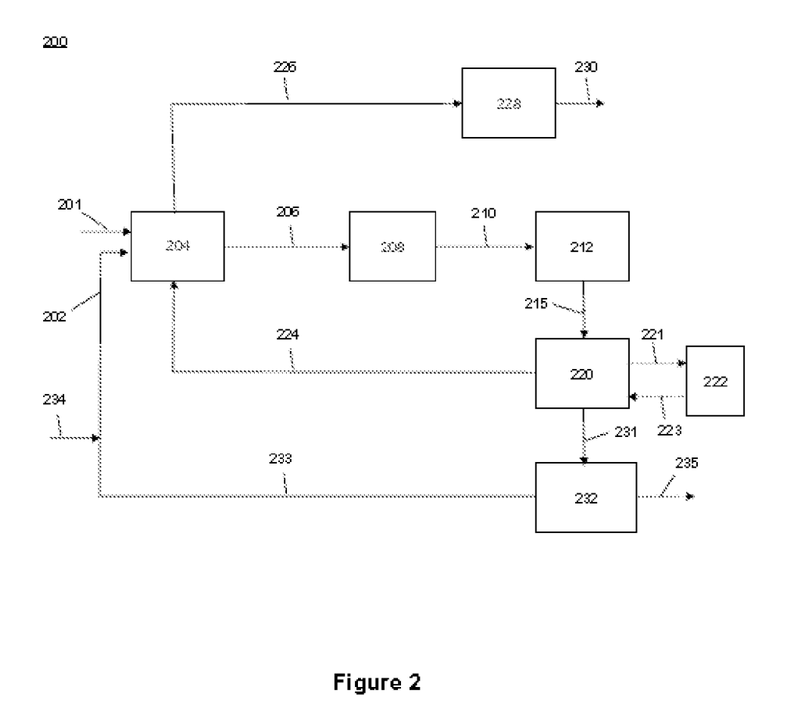
FIG. 2 is a block diagram relating to one exemplary configuration of system to process a hydrocarbon stream to produce products in accordance with the present techniques.

As a specific example of an embodiment of the present techniques, FIG. 2 is a block diagram relating to one exemplary configuration 200 of a pyrolysis system to process a hydrocarbon stream to produce various products in accordance with the present techniques. In this configuration, various units, such as a heat exchanger 204, a static mixer 208, a depressurization unit 212, a vaporization unit 220, a hydrate inhibitor separation unit 232 and a pyrolysis unit 228 are in fluid communication with each other. As noted above, this configuration 200 provides a mechanism to manage hydrate formation without the use of driers or other conventional systems in an enhanced manner.

To operate, the hydrocarbon stream is provided via line 201 to the heat exchanger 204. Along with the hydrocarbon stream, the hydrate inhibitor is provided via line 202 to the heat exchanger 204. The heat exchanger 204 may be a shell-in-tube heat exchanger that maintains the hydrocarbon stream separate from the portion of the first product (e.g., the vaporized stream) from the vaporization unit 220 being utilized to cool the hydrocarbon stream. The heat exchanger 204 may include one or more nozzles or other fluid addition mechanism to add the hydrate inhibitor to the hydrocarbon stream. The hydrocarbon stream and the hydrate inhibitor may be mixed together in the heat exchanger 204 in this configuration (e.g., via a nozzle of other fluid addition mechanism). However, in another configuration, the hydrocarbon stream and the hydrate inhibitor may be mixed upstream of the heat exchanger 204 and passed through a mixing unit, such as a static mixer, to blend the streams.

The cooled mixture stream is provided via line 206 to the static mixer 208. The static mixer 208 may include one or more of injection nozzles, baffles, trays and/or other suitable device. The static mixer 208 may be configured to force the intimate mixing of the hydrate inhibitor with the hydrocarbon stream to force the interaction of the components within the stream. Then, the mixture stream is provided via line 210 from the static mixer 208 to the depressurization unit 212. The depressurization unit 212 may include one or more valves, expanders, turbo expansion devices and/or other suitable depressurization units. The depressurization unit 212 may be utilized to reduce the pressure of the mixture stream from an initial pressure ($P_I$) to a depressed pressure ($P_D$). The depressurization of the mixture stream may involve one or more depressurization steps based on the pressure changes (e.g., hydrocarbon stream transport pressure and the pyrolysis unit feed pressure). As a result of the depressurization, the temperature of the mixture stream may change from an initial temperature to a lower depressed temperature, which may be the lowest temperature in the process. Preferably, the temperature of the mixture stream after depressurization is in the range of $H_D<T<H_I$. At the lower pressures and temperatures, the mixture stream may begin to partially vaporize and begin to auto-refrigerate during the depressurization step.

The depressurized mixture stream may be provided to the vaporization unit 220 via line 215. The vaporization unit 220 may be configured to (i) vaporize at least a portion of the remaining un-vaporized stream; and/or (ii) separate a first product from a second product. The first product includes at least a portion of the vapor phase of the mixture stream, which forms the first product, and the second product that includes the remaining portion of the stream, which may include the liquid phase of the mixture stream. To vaporize at least a portion of the mixture stream, the vaporization unit 220 may include a vaporization zone that includes a heat source, such as a burner or higher temperature fluid in a heat exchanger as compared to the mixture stream. As an example, a heat source 222 may provide a higher temperature fluid via lines 221 and 223 (e.g., a utility fluid at a temperature above the mixture stream temperature) to the vaporization unit 220 to provide heat via indirect contact with the mixture stream. For certain configurations, the vaporization unit 220 may be configured to maintain the mixture stream separate from the utility fluid being utilized to heat the depressurized mixture stream. The higher temperature fluid may be a utility fluid, such as water, ethane, ethylene or any other suitable fluid, and/or a stream that is associated with another portion within the pyrolysis system or another system at the facility, such as tower condenser service. For example, the utility fluid may include propylene refrigerant from a unit downstream of the pyrolysis unit 228, feed water being provided to or from a boiler or may include a stream from another process.

To separate the first product from the second product, the vaporization unit 220 may include a separation zone. The separation zone may include one or more flash drums, cyclone separation units, gravity separation units, or other suitable unit. The composition of the vapor phase leaving the separation zone of the vaporization unit 220 is substantially the same as the composition of the vapor phase entering the separation zone, and likewise the composition of the second product leaving the separation zone is substantially the same as the composition of the liquid phase and solids, if any, entering the separation zone. That is, the separation in the separation zone consists essentially of a physical separation of the vapor phase from the other phases entering the separation zone.

As an example, the vaporization unit 220 may include a hybrid design with front-end heat exchanger with integral drum. Specifically, the vaporization unit 220 may include a shell and tube heat exchanger in fluid communication with and coupled to a flash drum. The drum may include an outlet for vapor phase products (e.g., the first product) and an outlet for liquid products (e.g., the second product). As another example, the vaporization unit 220 may include one or more separate units coupled together via conduits. In particular, the vaporization unit 220 may include a stream vaporization unit (e.g., a heat exchanger) in fluid communication with a separation vessel (e.g., flash drum) to provide the separation. That is, the vaporization unit 220 may include a shell and tube heat exchanger coupled via a conduit to a separation drum, wherein the drum includes an outlet for vapor phase products (e.g., the first product) and an outlet for liquid products (e.g., the second product).

To operate, the hydrate inhibitor and water from the hydrocarbon stream should not vaporize for preferred separation in the drum. If the hydrocarbon stream is ethane along with water, the ethane is substantially vaporized in the heat exchanger. However, under transient conditions, any un-vaporized ethane from the heat exchanger (e.g., vaporization zone) is trapped in the drum (e.g., separation zone) and is eventually vaporized via contact with the fluids from the back end of the heat exchanger. The turbulence is minimal in the drum to allow the hydrate inhibitor and additional water (e.g., thermodynamic inhibitor and water in the stream) to settle from any liquid ethane phase. As a result, the heat exchanger may preferably vaporize ≥95 wt % or ≥99 wt % of the ethane in the stream and provide a separation that removes the ethane as the first product, while the hydrate inhibitor and water in the stream are removed as a second product.

Once separated, the first product may be heated upstream of the pyrolysis unit 228. Specifically, the first product may be provided to the heat exchanger 204 via line 224 to heat the first product in line 224 and cool the streams in the heat exchanger 204. Then, the first product may be heated in other heat exchangers (not shown) to further heat the first product to a predetermined pyrolysis feed temperature. Then, the first product may be provided to the pyrolysis unit 228 via line 226. The pyrolysis unit 228 is a conversion reactor that is utilized to thermally decompose the hydrocarbons in the first product into products, as is known in the art. The pyrolysis unit 228 may include a steam cracking furnace, partial oxidation reactor, regenerative reverse flow reactor or other suitable conversion unit, which may or may not include a catalyst. Examples of such pyrolysis units include U.S. Patent App. Pub. Nos. 20040004022; 20040004027; 20070191664; 20080300438 and/or 20090008292. As a specific example, the pyrolysis unit may be a steam cracking furnace that includes a convection section, a radiant section and a separator integrated into the convection section. As another example, the pyrolysis unit may be a regenerative reverse flow reactor. The pyrolysis products may be provided to other units via line 230. These units may include a fractionator to separate the pyrolysis product into various components or products by their respective boiling points and subsequently further processed into other products, such as polyethylene, as is known in the art.

The second product may be provided to the hydrate inhibitor separation unit 232 to separate a third product (e.g., a portion of the thermodynamic inhibitors) from a fourth product (e.g., the other fluids in second product). The hydrate inhibitor separation unit 232 may include one or more boilers, heat exchangers, a portion of the pyrolysis unit, or suitable combinations thereof, which may be coupled to a separation unit that may include a flash drum or vapor liquid separator. As an example, the hydrate inhibitor separation unit 232 may include a boiler, where the water may be converted to steam to separate the water from the thermodynamic inhibitors. The separation of the third product from the fourth product may be adjusted based on the desired concentration of thermodynamic inhibitors in the hydrate inhibitor, which is discussed further below. Also, in certain embodiments, the process may involve a separation that includes water with the thermodynamic inhibitor in the third product, or may include a process that removes substantially all of the water from the thermodynamic inhibitor. As such, additional water may also be supplied to the third process to provide certain concentrations of thermodynamic inhibitor in the third product.

The third product may be provided via line 233 alone or may be combined with an unprocessed amount of thermodynamic inhibitors provided via line 234 to form the hydrate inhibitor provided via line 202 to the heat exchanger 204. The fourth product may be provided via line 235 for further processing, such as water treatment or may be utilized in other processes as utility fluid.

As a prophetic example, the hydrocarbon stream may be a dense phase ethane (e.g., ethane in the super critical state), which may be provided in the temperature range of 70° F. to −20° F. (21.1° C. to −28.9° C.). The ethane is provided at an initial pressure ($P_I$) of 900 psig (6205 kPag) at a temperature of 70° F. (21.1° C.). Ethane has an initial hydrate formation point ($H_I$) that is 60° F. (15.5° C.) at the $P_I$ of 900 psig (6205 kPag). The dense phase ethane may include greater than 95 wt % ethane with the remaining stream being propane, methane and water. The hydrocarbon stream may be combined with a hydrate inhibitor that includes greater than 70 wt % thermodynamic inhibitor in an aqueous solution via nozzles in the front end of the heat exchanger 204. As a result of the addition of the hydrate inhibitor, the depressed hydrate formation point ($H_D$) for the mixture stream may be at a temperature of less than 0° F. (−17.8° C.) at $P_I$ of 900 psig (6205 kPag). The heat exchanger 204 may cool the mixture stream to a temperature of about 35° F. Then, the mixture stream may be provided to the static mixer 208 to further intermingle the components of the mixture stream. Following the static mixer, the pressure ($P_I$) of the mixture stream may be reduced in the depressurization unit 212, which may be a valve, to a depressed pressure ($P_D$), which may be about 200 psig (1379 kPag). As a result of the depressurization, ethane within the mixture stream may begin to vaporize and the temperature of the mixture stream may be depressed, which may be a temperature of −10° F. (−23.3° C.). The depressed hydrate formation point ($H_D$) for the $P_D$ of 200 psig (1379 kPag) at a temperature (T) less than −10° F. (−23.3° C.). As a result, hydrates should not form at these process conditions. Then, in the vaporization unit 220, the mixture stream may be heated to −1° F. (−18.3° C.) to further vaporize the ethane in the mixture stream. Then, the first product, which includes the vaporized ethane, may be separated from the second product, which includes water and thermodynamic inhibitors. The heated vaporized ethane is heated in the heat exchanger 204 to a temperature of 60° F. (15.5° C.), and then provided to the pyrolysis unit 228, which is a steam cracking unit. The second product may be provided to a hydrate inhibitor separation unit 232, which is a heat exchanger integrated with the pyrolysis furnace 228. In this heat exchanger, at least a portion of the water may be converted into steam and separated from the third product, which includes thermodynamic inhibitor, in a flash drum. The third product may be combined with additional thermodynamic inhibitor to form the hydrate inhibitor to be recycled to the process via line 202.

In this example configuration, hydrates may form as free water is knocked out in the cool down pass of heat exchanger 204 and across the depressurization unit 212 (e.g., the letdown valve). Once the ethane is in vaporization unit 220, the ethane begins to heat up and hydrate formation is less of a concern. The "cold" point in the example is at the letdown valve and so this is the location with the greatest potential for hydrate formation and sets the required thermodynamic inhibitor concentration in the hydrate inhibitor. To prevent hydrates, the hydrate inhibitor is mixed with the hydrocarbon stream and available to attach to the free water as it is formed in the stream. As may be appreciated, the hydrate inhibitor may be injected prior to the heat exchanger 204, at the inlet to the heat exchanger 204, and/or at or upstream of the inlet to the depressurization unit 212 (e.g., inlet of letdown valve).

As another example, the hydrocarbon stream may include greater than 90 wt % methane in the super critical state. In this configuration, the hydrocarbon stream may be provided in a temperature range of 70° F. to −40° F. (21.1° C. to −40° C.). The hydrocarbon stream may be provided at a $P_I$ of 1200 psig (8274 kPag) at a temperature of 65° F. (18.3° C.), and may be depressurized to a $P_D$ of 200 psig (1379 kPag). The hydrate formation point for methane is about 44.6° F. (7° C.) at the $P_I$ of 1200 psig (8274 kPag), while the hydrate formation point is about 17.6° F. (−8° C.) for $P_D$ of 200 psig (1379 kPag). This example may operate similar to the example above, but the vaporization may involve heating the stream to a temperature of 20° F. (−6.7° C.). Further, the first product, which includes the vaporized methane, may be heated in the heat exchanger 204 to a temperature of 60° F. (15.5° C.), and then provided to the pyrolysis unit 228, which is a regenerative reverse flow reactor that exposes at least a portion of the first product to temperatures in the range of 1500° C. to 1900° C.

Further, the hydrate inhibitor is preferably thoroughly mixed with the hydrocarbon stream to operate properly. That is, as the location for the hydrate formation problems is greatest at the depressurization unit 212, where the "cold" point exists for the system 200, the intermingling of the mixture streams is preferably upstream of the depressurization unit 212. This may involve having an adequate thermodynamic inhibitor concentration present in the hydrate inhibitor to achieve the hydrate temperature depression required, as noted further below.

Also, unlike NGL processes, the hydrocarbon stream is many times denser than a typical NGL stream. Accordingly, different mechanisms may be utilized to facilitate the blending of the hydrocarbon stream and the hydrate inhibitor. As an example, spray injection nozzles in a channel head may be utilized to ensure each tube of the heat exchanger 204 is provided with hydrate inhibitor to prevent hydrate plugging of individual tubes. A configuration may involve higher hydrate inhibitor flow rate per nozzle to penetrate the higher density fluid than is typically utilized for other applications. That is, the nozzle should be configured to handle fluids with density of greater than or equal to 20 lb/ft$^3$, or even greater than or equal to 25 lb/ft$^3$. Further, as noted above, the hydrate inhibitor may be provided to the hydrocarbon stream at a location upstream of the heat exchanger to facilitate the mixing of the streams. This may also involve the use of one or more mixing units (e.g., static mixers) to provide sufficient intermingling of the streams.

As noted above, the hydrate inhibitor may include a mixture of thermodynamic inhibitor and another fluid, such as water, for example. The concentration of thermodynamic inhibitor in the hydrate inhibitor or aqueous phase to achieve a specific hydrate temperature depression is well understood and documented in various references, such as Carroll, John, Natural Gas Hydrates: A Guide for Engineers (2nd Edition), Gulf Professional Publishing, (2009) p 119-122. Any of thermodynamic inhibitors may be utilized to achieve the temperature depression required, which may be calculated based on the hydrocarbon stream and the proposed configuration of equipment, as example of which is described below.

Figure 3:
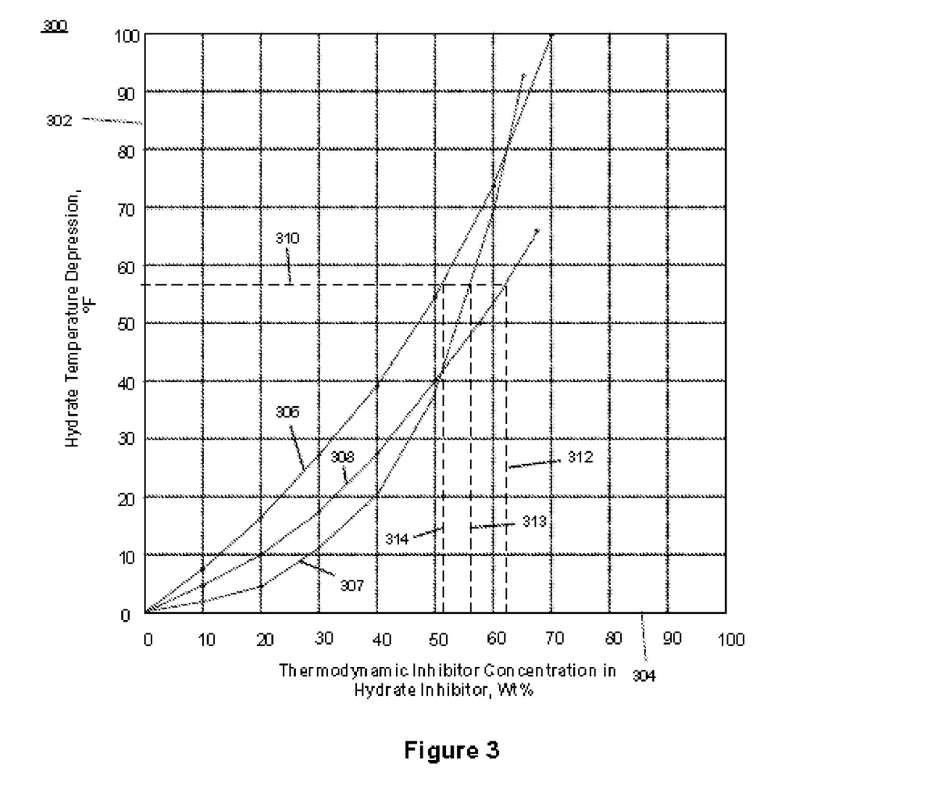
FIG. 3 is a diagram of hydrate temperature depression compared with hydrate inhibitor concentration in aqueous phase.

FIG. 3 is a diagram of hydrate temperature depression compared with thermodynamic inhibitor concentration in the hydrate inhibitor. In this diagram 300, certain values for the concentration of a thermodynamic inhibitor in wt % of the hydrate inhibitor are shown along the X-axis 304, while certain values of the hydrate depression temperatures (in ° F.) are shown along the Y-axis 302. The concentration of a thermodynamic inhibitor in wt % of the hydrate inhibitor for a given hydrate depression temperature are shown as curves, such as a MeOH curve 306, a TEG curve 307 and a MEG curve 308, in this diagram 300. As indicated in this diagram 300, different concentrations of thermodynamic inhibitor may be utilized to lower the hydrate formation point based on the temperature drop expected for the mixture stream.

As noted in the example above, if the hydrate temperature depression for a hydrocarbon stream may be 58° F. (14.4° C.), as indicated by dashed line 310, then the concentration of a thermodynamic inhibitor in wt % of the hydrate inhibitor is indicated for the different curves 306, 307 and 308. Specifically, for MeOH, the dashed line 314 intersects the MeOH curve 306 at a concentration of MeOH in the hydrate inhibitor of about 52 wt %. For TEG, the dashed line 313 intersects the TEG curve 307 at a concentration of TEG in the hydrate inhibitor of about 56 wt %. Similarly, for MEG, the dashed line 312 intersects the MEG curve 308 at a concentration of MEG in the hydrate inhibitor of about 62 wt %. As such, the amount of temperature drop for a stream may be utilized to calculate the specific thermodynamic inhibitor concentration in the hydrate inhibitor.

Based on the calculated concentration of the thermodynamic inhibitor, the process may involve using concentrations above those suggested by the respective thermodynamic inhibitor curve. That is, an amount may be selected for the recycle or addition of thermodynamic inhibitor to maintain the concentration levels within the hydrate inhibitor below the respective thermodynamic inhibitor curve. As an example, if the hydrocarbon stream is ethane and the thermodynamic inhibitor is MEG, the concentration of MEG in wt % of the hydrate inhibitor of about 62 wt % should be utilized to provide a 58° F. (14.4° C.) drop in the hydrate formation temperature. The process may utilize a concentration of MEG in wt % of the hydrate inhibitor of about 70 wt % to operate within a margin of error. Accordingly, the calculated concentration of thermodynamic inhibitor in wt % of the hydrate inhibitor may be greater than 110% and/or greater than 120% of the calculated amount for certain configurations, but less than or equal to 100 wt % of the hydrate inhibitor. That is, if the concentration of MEG is about 60 wt %, the amount utilized may be 68 wt % (for 110%) or 72 wt % (for 120%).

As an example, the compositions of the thermodynamic inhibitor and water in the streams are described below. For this example, the system may include a heat exchanger that combines the hydrocarbon stream with the hydrate inhibitor stream and cools the streams, a static mixer, a hybrid vaporizer unit, a hydrate inhibitor separation unit to separate the thermodynamic inhibitor from the second product, and a thermodynamic inhibitor valve coupled between the hydrate inhibitor separation unit and the heat exchanger. This configuration may be similar to the one provided in FIG. 2. The hydrocarbon stream may be a dense phase ethane stream that includes 9 pounds (lb) (4.1 kilograms (kg)) of $H_2O$ and 0 lb (0 kg) of MEG, which is the thermodynamic inhibitor for this example, while the hydrate inhibitor may include includes 500 lb (226.8 kg) of $H_2O$ and 1500 lb (680.4 kg) of MEG. That is, the concentration of the thermodynamic inhibitor in the hydrate inhibitor may be at least 75%. Downstream of the heat exchanger and upstream of the hybrid vaporizer unit, the composition may include 509 lb (230.9 kg) of $H_2O$ and 1500 lb (680.4 kg) of MEG. Downstream of the hybrid vaporizer unit, the first product may include 6 lb (2.7 kg) of $H_2O$ and 0 lb (0 kg) of MEG, while the remaining MEG and water are further processed in the hydrate inhibitor separation unit to provide the recycle stream, which may include the addition of MEG via the thermodynamic inhibitor valve for MEG lost or to adjust the concentration level of the MEG. As may be appreciated, the water in the hydrate inhibitor (e.g., 500 lb (226.8 kg) of $H_2O$) is larger than water present in the hydrocarbon stream (e.g., 9 lb (4.1 kg)). Accordingly, for this configuration, the thermodynamic inhibitor concentration in the hydrate inhibitor should control the temperature drop for the process.

As an alternative, as noted above, the hydrate inhibitor may include predominately thermodynamic inhibitor or any amount of thermodynamic inhibitor. These adjustments for amount of thermodynamic inhibitor in other embodiments may utilize the present techniques, as described herein, to compensate for the total water in the mixture stream (e.g., water from the hydrate inhibitor and the hydrocarbon steam) to provide the appropriate hydrate formation depression.

In addition, certain thermodynamic inhibitors may be preferred based on the specific configuration, hydrocarbon stream and/or process conditions. For instance, the vapor pressure of the thermodynamic inhibitor may be high, which would result in the vaporization of the thermodynamic inhibitor along with the hydrocarbons in the mixture stream. As an example, methanol has a high vapor pressure, which may result in the methanol being converted along with the first products separated in the vaporization unit from the second product. Specifically, if the hydrocarbon stream is ethane, 90 percent of injected methanol may be vaporized with the ethane, which may cause various contamination issues or may involve a separate separation step to remove the methanol.

This type of thermodynamic inhibitor may be useful for different configurations. The preferred thermodynamic inhibitor may depend upon the hydrate temperature depression (e.g., the temperature drop in the system), composition of the hydrocarbon stream and/or other aspects. To begin, the different thermodynamic inhibitors provide different temperature depressions based on the concentrations, as noted above. As an example, less MeOH may be used as compared to MEG and TEG. As such, less MeOH may be used as compared to MEG and TEG for certain hydrate temperature depressions. As another consideration, the use of a high vapor pressure thermodynamic inhibitor may involve an additional separation step following the separation of the first product from the second product. That is, an additional separation unit may be utilized to separate the thermodynamic inhibitor from the desired hydrocarbons in the first product. In other configurations, the thermodynamic inhibitor may be provided to the pyrolysis unit, as part of the process, which may pass through the system or be converted into products. As an example, less MeOH may be used as compared to MEG and TEG, but MeOH may present problems with the separation from the hydrocarbons being processed and involve additional separation steps.

Alternatively, other thermodynamic inhibitors may have a low vapor pressure, which would result in the thermodynamic inhibitor being removed as noted above for FIG. 2. As an example, certain glycol compounds, such as mono-ethylene glycol (MEG) and tri-ethylene glycol (TEG), have a lower vapor pressure and tend not to vaporize at the process conditions of ethane. As a result, the glycol compounds may be recovered and recycled, as noted above in FIG. 2.

Another factor to be considered for the selection of a thermodynamic inhibitor is the viscosity of the thermodynamic inhibitor. As an example, MEG has a lower viscosity than TEG, which assists the separation from any potential unvaporized hydrocarbons.

As noted above, certain operational parameters may be monitored and certain operational settings may be adjusted to provide the appropriate amount of hydrate inhibitor in the process. Specifically, the concentration of the thermodynamic inhibitors may be determined in the hydrate inhibitor and adjusted based on various operational parameters, which are monitored and stored in memory. The operational parameters may include operational data provided by various measuring devices or operational settings associated with the different units within the system 200. As an example, the operational parameters may include the temperature measurements, composition measurements and/or pressure measurements of the different fluids through the system 200.

Moreover, in one or more of the embodiments, a control mechanism may be utilized to provide the appropriate concentration of thermodynamic inhibitor in the hydrate inhibitor and to monitor for the formation of hydrates within the process. The control mechanism may include a process control unit coupled to one or more measurement devices that measure operational data (e.g., temperature, water or thermodynamic inhibitor content, composition, pressure, and the like) and one or more control units for adjusting settings (e.g., flow rate of thermodynamic inhibitor into the hydrate inhibitor, separation level in the separation unit and/or the like). The process control unit, measurement devices and/or control units may communicate with each other via a physical and/or wireless means. That is, the present techniques may involve monitoring certain operational data (e.g., measurements, parameters, and/or operational settings stored in the memory) and adjust physical settings to provide an enhanced process. Accordingly, a control mechanism may be utilized with this configuration to determine whether hydrates are forming within the process and to determine whether the appropriate concentration of thermodynamic inhibitor is being utilized in the process.

The process control unit may include a computer system along with one or more monitors and input/output components. The computer system may include memory to store sets of instructions and operational data and a processor to execute the instructions and access the operational data. The process control unit may include a display, a user interface device, communication components to communicate with the control units and measurement devices, and other suitable components. The instructions stored in the memory may include a set of instructions configured to obtain the operational data from one or more measurement devices, obtain the operational settings from one or more control units, calculate an indication to adjust the concentration of thermodynamic inhibitor, communicate adjustments to the operational settings for one or more control units. As an example, the set of instructions stored in memory may be configured to obtain measurements, such as pressure measurements, temperature measurements and composition or concentration measurements at various locations throughout the system, to determine whether the measurements indicate that hydrates may be forming within the flow paths of the system, to calculate an adjustment to the concentration of the thermodynamic inhibitor based on the measurements and/or the determination regarding hydrate formation, and/or communicate adjustments to control units based on the calculated concentration of the thermodynamic inhibitor.

Along with the process control unit, the control mechanism may include different types of measurement devices, such as one or more temperature measurement devices, pressure measurement devices and/or composition measurement devices that can measure water or thermodynamic inhibitor content, ethane content and/or other concentrations. Each of these measurement devices may include memory for storing instructions and operational data (e.g., measurements), a processor for executing the instructions and accessing and storing operational data, a sensor for obtaining measurements, and communication components to communicate with the process control unit and/or other units. The instructions stored in the memory may include a set of instructions configured to obtain the operational data from the one or more sensors and communicate measurements to the process control unit and/or other units. As an example, the temperature measurement device, which may include a thermocouple, may be configured to measure the temperature of the hydrocarbon stream prior to the heat exchanger 204, the mixture stream upstream of the static mixer 208 and/or upstream of the vaporization unit 220. The pressure measurement device, which may include a pressure sensor, may be configured to measure the pressure of the mixture stream prior to the depressurization unit 212, between the depressurization unit 212 and the vaporization unit 220 and/or upstream of the heat exchanger 204. The composition measurement device, which may include a nuclear magnetic resonance spectrometer (NMR), gas chromatograph (GC), specific gravity/boiling curve analyzer or a offline correlation of specific gravity and simulated distillation, may be configured to measure the water or thermodynamic inhibitor content of the third product downstream of the hydrate inhibitor separation unit 232, of the hydrate inhibitor upstream of the heat exchanger 204, and/or the hydrocarbon stream upstream of the heat exchanger 204.

The one or more control units may include different control units to adjust different physical settings. Each of these control units may include memory for storing instructions and operational data, a processor for executing the instructions and accessing and storing operational data, a control module to adjust a physical setting on a device (e.g., valve), and communication components to communicate with the process control unit and/or other units. The instructions stored in the memory may include a set of instructions configured to obtain the operational data from the process control unit and/or other units and communicate operational data and parameters to the control module. For example, a thermodynamic inhibitor flow control unit may be utilized or configured to adjust the amount of the thermodynamic inhibitor mixed with the third product from the hydrate inhibitor separation unit 232. That is, the thermodynamic inhibitor flow control unit may include one or more valves (e.g., a valve on line 234) to adjust the flow rate of the thermodynamic inhibitor being mixed with the third product. Also, a hydrocarbon stream control unit may be utilized and configured to adjust the flow rate of the hydrocarbon stream into the heat exchanger 204, while a hydrate inhibitor control unit may be utilized to control the flow of the hydrate inhibitor to the heat exchanger 204. A bypass control unit may be utilized and configured to adjust the temperature of utility fluid being provided to the vaporization unit 220.

As a specific example, the system 200 may include one or more process control unit, pressure measurement devices, and/or flow control units. The pressure measurement devices may be coupled to the inlet to the heat exchanger 204, the outlet of the heat exchanger 204, the outlet of the depressurization unit 212, along the line between the depressurization unit 212 and the vaporization unit 220, and/or at the inlet of the vaporization unit 220, while the flow control units may be coupled to the line 234 and configured to adjust the amount of thermodynamic inhibitor mixed with the third product or may be coupled to the line 202 to control the amount of hydrate inhibitor added to the hydrocarbon stream. The process control unit may be a computer system having a set of instructions in memory, which are configured to obtain pressure measurements from the pressure measurements from the pressure measurement device, to determine whether the pressure measurements indicate that hydrates may be forming within the system 200, to calculate an adjustment to the concentration of the thermodynamic inhibitor or to the concentration of the hydrate inhibitor based on the measurements and/or the determination regarding hydrate formation, and/or communicate adjustment to the flow control unit based on the calculated concentration of the thermodynamic inhibitor. The flow control unit may receive the adjustments and adjust the setting for the appropriate valve coupled to the flow control unit.

As yet another example, the system 200 may include one or more process control unit, temperature measurement devices, and/or flow control units. The temperature measurement devices may be coupled to the outlet of the depressurization unit 212, along the line between the depressurization unit 212 and the vaporization unit 220, and/or at the inlet of the vaporization unit 220, while the flow control units may be coupled to the line 234 and configured to adjust the amount of thermodynamic inhibitor mixed with the third product or may be coupled to the line 202 to control the amount of hydrate inhibitor added to the hydrocarbon stream. The process control unit may be a computer system having a set of instructions in memory, which are configured to obtain temperature measurements from the temperature measurement devices, to determine whether the temperature measurements indicate that hydrates may be forming within the system 200, to calculate an adjustment to the concentration of the thermodynamic inhibitor or to the concentration of the hydrate inhibitor based on the measurements and/or the determination regarding hydrate formation, and/or communicate adjustment to the flow control unit based on the calculated concentration of the thermodynamic inhibitor. The determination may include comparing the temperature measurements to a minimum temperature threshold for a specific concentration of thermodynamic inhibitor and/or a maximum temperature threshold for a specific concentration of thermodynamic inhibitor. Based on this comparison, the appropriate concentration of thermodynamic inhibitor may be calculated based on the equations and curves discussed above. The flow control unit may receive the adjustments and adjust the setting for the appropriate valve coupled to the flow control unit.

As yet still another example, the system 200 may include one or more process control unit, composition measurement devices, and/or flow control units. The composition measurement devices may be configured to measure the water or thermodynamic inhibitor content of the third product downstream of the hydrate inhibitor separation unit 232, of the hydrate inhibitor upstream of the heat exchanger 204, and/or the hydrocarbon stream upstream of the heat exchanger 204, while the flow control units may be coupled to the line 234 and configured to adjust the amount of thermodynamic inhibitor mixed with the third product or may be coupled to the line 202 to control the amount of hydrate inhibitor added to the hydrocarbon stream. The process control unit may be a computer system having a set of instructions in memory, which are configured to obtain temperature measurements from the temperature measurement devices, to determine whether the temperature measurements indicate that hydrates may be forming within the system 200, to calculate an adjustment to the concentration of the thermodynamic inhibitor or to the concentration of the hydrate inhibitor based on the measurements and/or the determination regarding hydrate formation, and/or communicate adjustment to the flow control unit based on the calculated concentration of the thermodynamic inhibitor. The determination may include comparing the temperature measurements to a minimum temperature threshold for a specific concentration of thermodynamic inhibitor and/or a maximum temperature threshold for a specific concentration of thermodynamic inhibitor. Based on this comparison, the appropriate concentration of thermodynamic inhibitor may be calculated based on the equations and curves discussed above. The flow control unit may receive the adjustments and adjust the setting for the appropriate valve coupled to the flow control unit.

As may be appreciated, the proposed hydrate suppression process may be utilized in other chemical processes, which involve temperatures greater than −40° F. (−40° C.) and where the water does not necessarily have to be removed for downstream processing. That is, a hydrate inhibitor may be useful in certain applications where driers are typically installed to reduce the risk associated with freezing or hydrate formation. As such, the hydrate temperature depression may be provided for various processes.

The adjustments to the hydrocarbon feed temperature may vary depending on the specific temperatures involved for the hydrocarbon feed and the dilution stream, if any.

Regardless of the specific operational data utilized, different configurations may be implemented to manage the hydrate formation in the system.

Further, it should be appreciated that the process control unit may include a computer system, one or more measuring devices and/or one or more control units that operate in real time, concurrently with the processing of the hydrocarbon, prior or during the processing of the hydrocarbon feed, or a combination thereof. Real time refers to the ability to observe operational data during the operation being performed, at or near in time with the actual operation being performed. Concurrently refers to data flow that has been delayed in some way, such as to allow a calculation of results or polling to provide the data within a specific time window.

Further, the process and system may include other embodiments, which are described below:

1. A method of processing a hydrocarbon stream comprising: providing a hydrocarbon stream having an initial hydrate formation point ($H_I$); adding a hydrate inhibitor to the hydrocarbon stream to form a mixture stream and lower the hydrate formation point from the initial hydrate formation point ($H_I$) of the hydrocarbon stream to a depressed hydrate formation point ($H_D$) of the mixture stream; depressurizing the mixture stream to adiabatically cool the mixture stream to a temperature (T), wherein the $H_D < T < H_I$; vaporizing at least a portion of the mixture stream; and separating a first product that includes at least a portion of the vaporized portion of the mixture stream from a second product that includes at least a portion of the unvaporized portion of the mixture stream.

2. The method of paragraph 1, comprising passing the mixture stream through a static mixer to intermingle the compounds in the mixture stream upstream of the depressurizing.

3. The method of any one of paragraphs 1 to 2, wherein the vaporizing comprises heating the mixture stream to a temperature sufficient to vaporize at least a portion of the mixture stream.

4. The method of any one of paragraphs 1 to 3, further comprising processing at least a portion of the first product in a pyrolysis reactor to produce $C_2$ unsaturates.

5. The method of paragraph 4, further comprising: cooling the mixture stream upstream of the depressurizing by passing the mixture stream through a first side of a heat exchanger; and heating at least a portion of the first product upstream of the pyrolysis reactor by passing the portion of the first product through a second side of the heat exchanger upstream of the pyrolysis reactor.

6. The method of any one of paragraphs 4 to 5, wherein the processing involves heating the at least a portion of the first product to temperatures in the range of 500° C. to 880° C. to produce the $C_2$ unsaturates.

7. The method of any one of paragraphs 4 to 5, wherein the processing involves heating the at least a portion of the first product to temperatures in the range of 1200° C. to 2000° C. to produce the $C_2$ unsaturates.

8. The method of any one of paragraphs 1 to 7, wherein the hydrocarbon stream is at a pressure in the range of 700 psia to 1100 psia (4826 kPaa to 7584 kPaa) or at a pressure sufficient to be in the super critical state, wherein when the pressure is reduced it may vaporize and/or auto-refrigerate.

9. The method of any one of paragraphs 1 to 8, wherein the depressurizing comprises reducing the pressure of the mixture stream to pressure in the range of 50 psia to 400 psia (345 kPaa to 2758 kPaa).

10. The method of any one of paragraphs 1 to 9, wherein depressurizing comprises reducing the temperature to a sufficiently cold temperature to recover energy, which may include reducing the temperature of the mixture stream to a temperature in the range of 20° F. to −20° F. (−6.7° C. to −28.9° C.).

11. The method of any one of paragraphs 1 to 10, wherein hydrocarbon stream comprises ≥90 wt % ethane.

12. The method of paragraph 11, wherein the vaporizing comprises heating the mixture stream to vaporize ≥90 wt % of the ethane in the mixture stream.

13. The method of any one of paragraphs 1 to 10, wherein hydrocarbon stream comprises ≥90 wt % methane.

14. The method of any one of paragraphs 1 to 13, wherein the hydrate inhibitor has a concentration of thermodynamic inhibitor that is in the range of 60 wt % to 100 wt % of the hydrate inhibitor.

15. The method of any one of paragraphs 1 to 14, wherein the hydrate inhibitor comprises one or more of mono-ethylene glycol (MEG) and tri-ethylene glycol (TEG).

16. A hydrocarbon processing system comprising: a mixing unit configured to receive a hydrocarbon stream and a hydrate inhibitor and combine the streams together into a mixture stream; a depressurization unit in fluid communication with the mixing unit and configured to reduce the pressure of the mixture steam; a vaporization unit in fluid communication with the depressurization unit and configured to: vaporize at least a portion of the hydrocarbons in the depressurized mixture stream (e.g., via thermal exposure); a separation unit in fluid communication with the vaporization unit and configured to separate a first product comprising at least a portion of the vaporized hydrocarbons stream and a second product stream comprising the hydrate inhibitor.

17. The system of paragraph 16, further comprising a pyrolysis unit downstream of and in fluid communication with the separation unit and configured to process at least a portion of the first product to produce $C_2$ unsaturates.

18. The system of any one of paragraphs 16 to 17, wherein the vaporization unit and the separation unit are located in the same vessel.

19. The system of any one of paragraphs 16 to 18, further comprising a heat exchanger, upstream and in fluid communication with the depressurization unit, wherein the heat exchanger is configured to cool the hydrocarbon stream or mixture stream via indirect heat transfer with a utility fluid.

20. The system of paragraph 19, wherein the utility fluid comprises at least a portion of the first product and the heat exchanger is configured to heat the first product upstream of a pyrolysis unit.

21. The system of any one of paragraphs 16 to 20, wherein the depressurization unit is an expander valve configured to adjust the pressure from an upstream pressure in the range of 700 psia to 1100 psia (4826 kPaa to 7584 kPaa) to a downstream pressure in the range of 100 psia to 300 psia (689 kPaa to 2068 kPaa).

22. The system of any one of paragraphs 16 to 17, wherein the mixing unit comprises a heat exchanger having nozzles disposed in an upstream portion of the heat exchanger, the nozzles being configured to intermingle the hydrate inhibitor with the hydrocarbon stream.

23. The system of any one of paragraphs 16 to 22, comprising a process control unit in communication with one or more control units and one or more measurement devices, wherein the process control unit is configured to adjust an amount of thermodynamic inhibitor in the hydrate inhibitor.

24. The system of paragraph 23, wherein the one or more measurement devices is coupled to a line upstream of an inlet or at the inlet of the depressurization unit and configured to communicate pressure data to the process control unit.

25. The system of paragraph 23, wherein the process control unit includes a processor, set of instructions stored in memory and when executed by a processor are configured to: (i) receive the pressure data; (ii) determine an amount of the thermodynamic inhibitor in the hydrate inhibitor; and (iii) indicate an adjustment of the amount of the thermodynamic inhibitor in the hydrate inhibitor.

The foregoing application is directed to particular embodiments of the present techniques for the purpose of illustrating it. It will be apparent, however, to one skilled in the art, that many modifications and variations to the embodiments described herein are possible. Further, some embodiments may be preferably performed at least partly on a computer, i.e., computer-implemented embodiments of the present inventive method are preferred, but not essential. All such modifications and variations are intended to be within the scope of the present invention, as defined in the appended claims.

What is claimed is:

1. A method of processing a hydrocarbon stream comprising:
    providing a hydrocarbon stream having an initial hydrate formation point ($H_I$);
    adding a hydrate inhibitor to the hydrocarbon stream to form a mixture stream and lower the hydrate formation point from the initial hydrate formation point ($H_I$) of the hydrocarbon stream to a depressed hydrate formation point ($H_D$) of the mixture stream;
    cooling the mixture stream by passing the mixture stream through a first side of a heat exchanger;
    depressurizing the mixture stream to adiabatically cool the mixture stream to a temperature (T), wherein $H_D<T<H_I$;
    vaporizing at least a portion of the mixture stream;
    separating a first product that includes at least a portion of the vaporized portion of the mixture stream from a second product that includes at least a portion of the unvaporized portion of the mixture stream;

heating at least a portion of the first product by passing the portion of the first product through a second side of the heat exchanger; and processing at least a portion of the first product in a pyrolysis reactor to produce C2 unsaturates.

2. The method of claim 1, comprising passing the mixture stream through a static mixer to intermingle the compounds in the mixture stream upstream of the depressurizing.

3. The method of claim 1, wherein the vaporizing comprises heating the mixture stream to a temperature sufficient to vaporize at least a portion of the mixture stream.

4. The method of claim 1, wherein the processing involves heating the at least a portion of the first product to temperatures in the range of 500° C. to 880° C. to produce the $C_2$ unsaturates.

5. The method of claim 4, wherein the processing involves heating the at least a portion of the first product to temperatures in the range of 1200° C. to 2000° C. to produce the $C_2$ unsaturates.

6. The method of claim 1, wherein the hydrocarbon stream is at a pressure in the range of 700 psia to 1100 psia (4826 kPaa to 7584 kPaa).

7. The method of claim 1, wherein the depressurizing comprises reducing the pressure of the mixture stream to pressure in the range of 50 psia to 400 psia (345 kPaa to 2758 kPaa).

8. The method of claim 1, wherein depressurizing comprises reducing the temperature of the mixture stream to a temperature in the range of 20° F. to −20° F. (−6.7° C. to −28.9° C.).

9. The method of claim 1, wherein hydrocarbon stream comprises≥90 wt % ethane.

10. The method of claim 9, wherein the vaporizing comprises heating the mixture stream to vaporize≥90 wt % of the ethane in the mixture stream.

11. The method of claim 1, wherein hydrocarbon stream comprises≥90 wt % methane.

12. The method of claim 1, wherein the hydrate inhibitor has a concentration of thermodynamic inhibitor that is in the range of 60 wt % to 100 wt % of the hydrate inhibitor.

13. The method of claim 1, wherein the hydrate inhibitor comprises one or more of mono-ethylene glycol (MEG) and tri-ethylene glycol (TEG).

\* \* \* \* \*